United States Patent [19]
Sokol

[11] 3,986,825
[45] Oct. 19, 1976

[54] HAIR COLORING COMPOSITION CONTAINING WATER-SOLUBLE AMINO AND QUATERNARY AMMONIUM POLYMERS

[75] Inventor: Phillip E. Sokol, Chicago, Ill.

[73] Assignee: The Gillette Company, Boston, Mass.

[22] Filed: May 14, 1975

[21] Appl. No.: 577,616

Related U.S. Application Data

[60] Division of Ser. No. 267,664, June 29, 1972, Pat. No. 3,912,808, which is a continuation-in-part of Ser. No. 14,205, Feb. 25, 1970, abandoned.

[52] U.S. Cl. .......... 8/10.1; 8/10; 8/10.2; 8/11; 8/32; 8/111; 8/127.51; 424/DIG. 1; 424/DIG. 2; 424/Dig. 3; 424/62; 424/70; 424/71; 424/72; 424/78; 424/81
[51] Int. Cl.$^2$ .......... A61K 7/13
[58] Field of Search .......... 8/10.1, 10.2, 10, 11, 8/32

[56] References Cited

UNITED STATES PATENTS

| | | | |
|---|---|---|---|
| 2,926,161 | 2/1960 | Butler et al. | 260/89.7 N |
| 3,253,980 | 5/1966 | Klinge et al. | 8/10.2 |
| 3,288,770 | 11/1966 | Butler | 260/89.7 N |
| 3,516,778 | 6/1970 | Brunner | 8/10.2 |
| 3,539,684 | 11/1970 | Hoover | 424/78 |
| 3,580,853 | 5/1971 | Parran | 424/78 X |

*Primary Examiner*—James O. Thomas, Jr.
*Assistant Examiner*—Vera C. Clarke

[57] ABSTRACT

A hair treating composition containing, in addition to a hair coloring agent, a water soluble secondary or tertiary amine polymer or a polymer of diallylamine or a quaternary polymer of diallyldialkylammonium salts which improves the surface characteristics of hair.

9 Claims, No Drawings

HAIR COLORING COMPOSITION CONTAINING WATER-SOLUBLE AMINO AND QUATERNARY AMMONIUM POLYMERS

This is a division of application Ser. No. 267,664, filed June 29, 1972, now U.S. Pat. No. 3,912,808; which application is a continuation-in-part of application Serial No. 14,205 filed Feb. 25, 1970, abandoned.

This invention relates to hair treating compositions for bleaching, waving or straightening, or coloring or dyeing hair and more specifically to such compositions containing high molecular weight water soluble polymers having a multiplicity of amino or of quaternary salt groups.

Modern day living results in exposure of individuals to increasing amounts of sunlight, chlorine water, harsh detergents and chemical specialty products. Becuase of this, hair treating products must be capable of leaving the hair with luster and softness while overcoming natural or induced harshness and dryness. This is in addition to a product's primary purpose whether it be to impart or maintain a hair style or to alter the natural color of the hair. There is, in each case, the corollary requirement that the hair be left with an improved appearance and feel. In those types of products where the hair is subjected to chemical reaction, it is important that the cosmetic be capable of restoring the hair as nearly as possible to its original state in relation to the feel of the hair, and frequently by its ease of combing.

There have been in the past several means of achieving this end. One of the simplest means of doing so has been to dissolve a conditioning material in a suitable solvent or vehicle. In some cosmetic forms, after application, the evaporation of solvent deposits the conditioning material. This method has been useful in the deposition of natural gums, certain of the synthetic polymers, and a few protein derivatives. A shortcoming of such systems, when aqueous, is that any such material that can be dissolved in water is equally subject to subsequent removal by simple washing. Water insoluble materials deposited on hair from organic solvent, while more resistant to water removal, require that the hair be subjected to the reaction of organic solvent materials capable themselves of extracting natural constituents of hair. Non-aqueous oleaginous mixtures have sometimes been used to deposit coatings of conditioning materials on hair. The standard hot oil treatment for hair and some hair grooms are representative. Such oil coatings, however, whether of mineral, animal or vegetable origin, are generally too greasy to satisfy modern tastes. Application of conditioning materials to hair from emulsion systems is often practiced enabling many materials to be used which would otherwise be difficult to apply. As in the previously indicated case of application from aqueous solvent systems, the deposited film is generally easily removable by simple water washing, the original emulsifying materials present in the composition also remaining behind to reduce the binding potential of the conditioning material to hair.

One of the more interesting and most widely used means for overcoming a harsh feeling in human hair is by the deposition of cationic materials which are absorbed by the protein structure of the substrate. Especially useful have been the cationic fatty quaternary compounds having fatty chain lengths of approximately 8 to 18 carbon atoms. These materials which form the basis of many of the conditioning hair rinse products found on the market, though substantive to skin and hair, cannot withstand, to any substantial extent, the action of most detergent materials used for personal cleansing. While these materials are an improvement over the older modes of conditioning described above, they can soften the hair excessively leaving it unmanageable and with a lack of body. It has not generally been found helpful to simply reduce the concentration of the quaternary material since to do so would reduce the combing benefits and/or conditioning properties imparted by such products to the hair. Furthermore, because many of the most widely used products for treating hair contain anionic surfactants and because cationic materials are usually inactivated by reaction with anionic surfactants, it is customary to employ cationic materials only as a separate composition such as a post shampoo rinse separately applied. There has been disclosed another means of depositing conditioning materials on hair. U.S. Pat. No. 3,313,734 and Canadian Pat. No. 762,893 describe cosmetic compositions containing certain polymers having cationic sites. The compositions yield a fine precipitate of the polymer components upon dilution with water. This precipitate adheres to the surface of the hair shaft, thereby altering surface properties of the hair fibers. This effect, as described in the above patents, is limited however to shampoo compositions and produces in many instances an undesirably heavy deposit of material which leaves the hair feeling coated and unclean.

It has now been discovered that the surface characteristics of hair can be modified and its condition improved by applying thereto a composition containing certain water soluble polymers containing secondary and tertiary amino or quaternary ammonium groups. These polymers are incorporated in the hair treating composition itself instead of being used in the form of separate solutions separately applied. The hair treating composition in each case includes in addition to water and the water-soluble polymer (as defined below) a coloring agent i.e. a hair dye or hair dye precursor; or a hair waving or straightening agent such as a reducing agent capable of breaking the disulfide linkages in hair keratin; or a peroxide such as hydrogen peroxide in the case of hair bleaching compositions or neutralizing compositions (for use in conjunction with waving or straightening compositions). Also present in the case of the hair coloring and hair bleaching compositions are a surface active agent such as a soap or detergent and sufficient water miscible aliphatic hydroxylated solvent (or a mixture of such solvent with a water-soluble salt inert to the ingredients and to hair) to maintain the composition homogeneous i.e. in a single phase.

The polymers are equally effective when an anionic surface active agent such as soap, etc. is present as when only cationic, nonionic, or ampholytic agents are present despite the fact that ionic interaction would be expected to lead to the formation of an inactive and insoluble catan wax. The polymer can be used effectively in amounts ranging upwardly from 0.5% by weight of the total composition. There is no critical upper limit to the amount of polymer which may be present, and amounts as great as 40% by weight of the composition or even more may be used, particularly when application of the composition to the hair is followed by a water rinse. If the composition is supplied in such concentrated form, however, it is generally desirable to dilute it with water to a polymer content of 0.5 to 15% by weight before use. The compositions in which the polymers may be effectively employed may vary widely in acid or base content, having a pH, when in water, from 1.5 to 11.5. The polymers are effective to alter the surface characteristics of the hair and maintain the desired conditioned effect even though the application of the composition is followed, intentionally or unintentionally, by a water rinse. Indeed, the conditioning effect produced by incorporating these polymers in a hair treating composition is remarkably durable, persisting in many cases through several successive rinses and even through successive washings with a conventional detergent or shampoo composition. This is true even in the case of hair coloring and hair bleaching compositions which contain soap or detergent which in itself would be expected to remove the polymer even if no shampoo were subsequently used.

In the hair coloring compositions of the present invention the coloring agents may be any of the known acidic, basic, or disperse dyes or oxidation dye intermediates; they may be present in any effective amount ranging from 0.03 to 10% by weight of the total composition, depending on the type of dye and the desired color result, as is well known to those skilled in the art. When the coloring agent is an oxidative dye intermediate, it is usually desirable to mix with the composition before applying it to the hair an oxidizing agent such as hydrogen peroxide, sodium peroxide, urea hydrogen peroxide or the like, in accordance with conventional practice, in an amount effective to develop the desired color.

The hair bleaching compositions contain in aqueous solution an oxidizing agent such as hydrogen peroxide or urea hydrogen peroxide together with conventional stabilizers such as phenacetin and/or sodium stannate together, if desired, with a suitable conventional buffer to maintain the pH at the desired level of 2.5 to 6.5. The amount of oxidizing agent, in accordance with conventional practice, may be from 0.5 to 20 % by weight of the total composition.

The hair waving and straightening compositions of the present invention contain aqueous solutions of reducing agents capable of reducing the disulfide linkages in hair keratin, of which many are well known such as water soluble mercaptans e.g. sodium or ammonium thioglycolate, magnesium thioglycolate, thioglycerol, sodium or potassium borohydride, sodium or ammonium sulfite, etc. The amount of such reducing agent, as is well known, may be from 0.5 to 10% by weight of the total composition. A variety of conventional additives for such compositions may also be present.

The neutralizer compositions of the present invention, which are used for applying to the waved or straightened hair to restore the disulfide linkages in the hair keratin, contain in aqueous solution any of the oxidizing agents conventionally employed for this purpose, such as hydrogen peroxide, urea hydrogen peroxide, sodium carbonate peroxide, sodium or potassium bromate, sodium perborate, or sodium hypochlorite; the neutralizer compositions used with sulfite waving or straightening composition may contain simply sodium sesquicarbonate instead of an oxidizing agent.

The surface active agent present as an essential ingredient of the hair coloring or hair bleaching composition may be a soap, i.e. an alkali metal, ammonium or amine salt of a long chain aliphatic acid, particularly a fatty acid, such as the sodium, potassium, lithium or ammonium salts or the salts of such amines as mono-, di-, or tri-ethanolamine, 2-amino-1-butanol, 2-amino-2-methyl-1-propanol, diethylamine, mono- and diisopropanolamine, polyglycolamine, N-ethylmorpholine with such acids as capric, undecylic, lauric, myristic, palmitic, stearic, oleic, linoleic, ricinoleic, dimer or trimer acids produced by polymerization of $C_{18}$ fatty acids, hydrogenated rosin acids, lanolin acids, phenylstearic acid, coconut fatty acids, tallow fatty acids, or castor fatty acids including hydroxyricinoleic acid and the like. The surface active agent may also be an anionic material such as sodium di-(2-ethylhexyl) phosphate dioctyl sodium sulfosuccinate, sodium dodecylbenzenesulfonate, sodium lauryl sulfate, or disodium ethoxylated alcohol half ester of sulfosuccinic acid. Cationic surface active agents can also be used, such as stearyldimethylbenzylammonium chloride, stearic aminoamide, dimethyldialkylammonium chlorides in which each alkyl group has from 8 to 18 carbon atoms, polyethoxylated quaternary ammonium salts, amidoamine oxide derivative of lauric acid, or cetylpyridinium chloride. Among nonionic surface active agents which can be used are various condensates of alkylene oxides, e.g. ethylene oxide or propylene oxide with other molecules, each condensate molecule containing from 5 to 500 alkylene oxide units, such as octylphenoxypolyethoxyethanol, condensates of ethylene oxide with hydrophobic bases formed by condensing propylene oxide with propylene glycol, mono- and diglycerides of long chain fatty acids, sorbitan esters of long chain fatty acids, polyoxyethylene sorbitan monolaurate, monopalmitate or monostearate, polyoxyethylene lauryl ether, polyoxyethylene stearyl ether, lauric diethanolamide, dimethyloctadecylamine oxide, nonylphenylpolyethylene glycol ether, ethylene oxide condensates with long chain fatty amides, acetylated lanolin alcohols, or coconut fatty acid alkanolamides. Amphoteric surface active agents useful in the compositions of the present invention include imidazoline derivatives made by condensing polyamines with long chain fatty acids including lauric, capric, oleic and stearic sold under the trade name Miranol in the form of various salts such as the potassium, sodium, mono-, di-, or triethanolamine or isopropanolamine salts, N-coco-beta-aminopropionic acid or its sodium salt, disodium N-lauryl-beta-iminodipropionate; N-lauryl/myristyl-beta-aminopropionic acid, or a complex polyalkylamido imidazolinium sulfate sold under the trade name Soromine CAZ-75. Any of these surface active agents may be present as an optional ingredient in the hair waving or straightening compositions or neutralizing compositions of the present invention. The surface active agents can be used in amounts from 0.1 to 50% by weight of the total composition, preferably from 0.3 to 25% by weight.

When a surface active agent is present in any of the compositions, there must also be present sufficient water miscible hydroxylated organic primarily aliphatic solvent, or a mixture of such solvent with inert water-soluble salt, to solubilize all of the ingredients. Among suitable solvents are ethanol, isopropanol, benzyl alcohol, hexylene glycol, hexanol, 2-methylpentanol, 2-ethylbutanol, diethylene glycol, tetraethylene glycol, propylene glycol, 1,5-pentanediol, polyethylene glycol, glycol ethers such as 2-ethoxyethanol, 2-phenoxyethanol, monoethylether of diethylene glycol, monobutyl ether of diethylene glycol, monobutyl ether of diethylene glycol, monobutyl ether of 1.2-propanediol, monomethyl ether of dipropylene glycol, or 1-butoxyethoxy-2-propanol. The minimum amount of such solvent needed to ensure homogeneity will vary depending upon the identity and quantity of other ingredients present but in general may range from 1 to 90% by weight of the total composition.

The water soluble salts which can be used in conjunction with the hydroxyl-containing solvent to increase its effectiveness include those which are chemically inert to the remaining ingredients of the composition as well as to the hair such as the sodium, potassium, lithium, ammonium or lower alkanolamine chlorides, bromides, sulfates, or acetates. They can be used in amounts from 0.01 to 15% by weight of the total composition, preferably from 0.05 to 5% by weight.

The polymers useful in the present invention are high molecular weight water-soluble amino and quaternary ammonium homopolymers and copolymers having as constituents of the chain or backbone of the polymer molecule (apart from end groups which terminate each such chain and which have no important effect upon the properties and characteristics of the polymer) units of the following formulas:

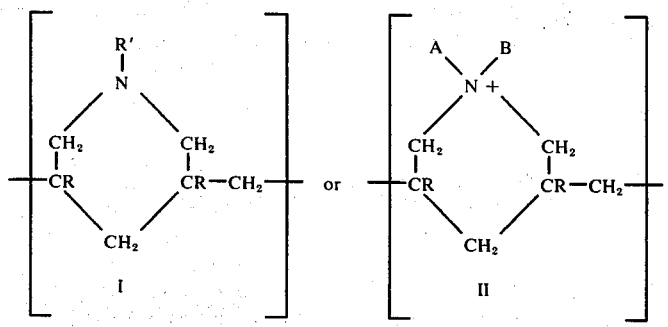

where R is hydrogen or methyl; R' is hydrogen, or an alkyl group having one to twenty-two carbon atoms, or a lower hydroxyalkyl group having from one to five carbon atoms, or a lower alkyl group containing a terminal amido group such as beta-propionamido; and wherein A and B are independently (i.e. either both the same or different) alkyl groups having one to twenty-two carbon atoms, lower hydroxyalkyl groups having from one to five carbon atoms, and lower alkyl groups containing terminal amido groups such as beta-propionamido; and wherein A and B together with N are piperidinyl or morpholinyl groups. Salts of Polymer I such as the hydrochloride, hydrobromide or sulfate are the full equivalent of Polymer I. In the case of both the polymer of Formula I and the polymer of Formula II the preferred homopolymers and copolymers are those in which R is hydrogen; and in the case of the polymer of Formula II the preferred homopolymers and copolymers are those in which A and B are independently lower alkyl groups having from 1 to 5 carbon atoms or in which A and B form together with nitrogen atom a piperidinium or a morpholinium group. These linear homopolymers and copolymers have a molecular weight from about 20,000 to 3,000,000. In the case of homopolymers, all of the units in the polymer chain are identical, while in the case of copolymers, the units, while having the structure defined above, are not all identical to each other and in addition, may contain the structures of acrylamide or diacetone acrylamide as described below. Any of a wide variety of nontoxic or cosmetically acceptable anions, organic as well as inorganic, may be present in the polymer and associated with the quaternary ammonium cationic groups, among which are, for example, acetate, borate, bromide, chloride, citrate, tartrate, bisulfate, bisulfite, sulfate, phosphate, and succinate. The homopolymers and copolymers of Formula I can be prepared as described in Butler et al U.S. Pat. No. 2,926,161 by polymerizing the appropriate diallylamine or amine salt. The homopolymers and copolymers of Formula II can be made by polymerizing diallyldialkylammonium chloride or bromide or other appropriate diallyl monomeric ammonium salts using a free radical generating polymerization catalyst such as a peroxide, then using an anion exchange column technique for exchanging the anion, if desired, and are described in U.S. Pat. Nos. 3,288,770 and 3,412,019. If a polymer of a chloride is dissolved in an aqueous solution or in a cosmetic base containing salts of any other anions, of course, the resulting solution contains both anions, each being associated to some extent with the quaternary ammonium groups of the polymer. Other monomers which can be copolymerized with diallylamine or with the desired diallylammonium salt to form copolymers containing units of Formula I or II include acrylamide and diacetone acrylamide. The polymer units derived from acrylamide have the structure

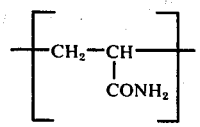

while those derived from diacetone acrylamide have the structure

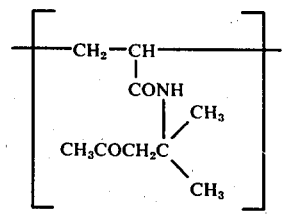

The amount of these acrylamide-type monomers incorporated in the copolymer may vary from 5% to 95% by weight of the total monomers; The copolymers can be made by subjecting the mixture of monomers to the same polymerization conditions as used in making the homopolymers. It generally makes no difference, so far as the present invention is concerned, whether the polymer or copolymer containing a particular desired anion or combination of anions is prepared in pure form before being mixed with the hair treating composition or whether the desired anions are introduced into the composition in the form of other salts. It is usually most convenient to employ the least expensive salt of the polymer which is readily available, regardless of the anion which it contains, and add the desired anions in the form of other less expensive salts. Hair treating compositions, as is well known, contain any of a wide variety of non-toxic anions, numerous examples of which are given herein. Particularly preferred is a polymer of a diallyldimethylammonium salt, that is, a polymer having repeating units of the formula given above where A and B are both methyl groups, all of the units being identical.

The following specific examples are intended to illustrate more fully the nature of the present invention without acting as a limitation upon its scope.

EXAMPLE 1

A conventional hair straightening lotion base was prepared having the following composition:

| Ingredient | Weight Percent |
| --- | --- |
| Ammonium bisulfite | 10.0 |
| Urea | 15.0 |
| Isopropanol | 4.0 |
| Hydroxyethylcellulose | 1.0 |
| Ammonium hydroxide to pH | 7.1 |
| Water to | 100.0 |

To one portion of the lotion was added 0.5% by weight of a polymer of diallyldimethylammonium chloride in the form of a 40% by weight aqueous solution having a viscosity of about 12,500 centipoises. Samples of the lotion with and without the added polymer were then employed to treat separate heads of hair under identical conditions, viz. application to clean hair and allowing to stand 20 minutes covered with a turban, application of additional lotion and allowing to stand for another 20 minute period covered with a turban, rinsing with water, applying a neutralizer a 4.5% aqueous solution of sodium sesquicarbonate dihydrate, and finally rinsing with water. It was found that the hair treated with the polymer-containing lotion was soft, lustrous and easy to comb both wet and dry as contrasted to the harsh feeling, difficult-to-comb hair resulting from the other lotion. The difference was still apparent after four weeks and several intervening shampoos. When as little as 0.05% of the polymer or as much as 2.0% were used, the results were very similar.

It has been found that the presence of relatively large quantities of inorganic salts commonly employed in cosmetic bases, such as sodium carbonate, sodium sulfate, sodium phosphate, or sodium tripolyphosphate has little or no effect upon the conditioning properties of a 10% by weight aqueous solution of a polymer of diallyl dimethyl ammonium chloride which has, in the form of a 40% by weight aqueous solution, a viscosity of 5000cps. Similar results were observed in the case of a 10% solution of a higher molecular weight polymer of the same species which exhibited a viscosity of 130,000 cps. in 40% aqueous solution.

EXAMPLE 2

Results similar to those obtained in EXAMPLE 1 were obtained by dissolving 2% by weight of the same polymer in the neutralizer solution instead of mixing polymer with the straightening lotion.

EXAMPLE 3

A hair waving lotion base was prepared having the following composition:

| Ingredient | Weight Percent |
| --- | --- |
| Ammonium thioglycolate | 7.8 |
| Diisopropanolamine | 6.7 |
| Polyoxyethylene(25)oxypropylene(5) monostearate | 0.5 |
| Perfume | 0.125 |
| Water to | 100.0 |

To one portion of the lotion was added 0.5% by weight of the polymer used in Example 1. Samples of the lotion with and without the added polymer were then employed to treat separate heads of hair under identical conditions, viz. application of the lotion of hair previously shampooed, winding of the hair on curlers, application of additional lotion to the hair and allowing to stand for 15 minutes, rinsing with water and allowing to stand covered with a turban for 30 minutes. A neutralizer consisting of an aqueous solution containing 1.2% hydrogen peroxide and 0.05% of stearyl dimethyl benzyl ammonium chloride was then applied to the hair on the curlers, the hair was removed from the curlers and the neutralizer again applied. The hair waved with the lotion containing the polymer was soft, lustrous, and easy to comb both wet and dry in contrast to the hair waved with the other lotion which was harsh, difficult to comb, and readily tangled. The marked difference in conditioning or surface characteristics of the hair persisted even after both heads had been subjected to six successive shampoos.

Similar results were obtained by dissolving the polymer in the neutralizer instead of in the lotion, as in Example 2.

EXAMPLE 4

A hair bleaching base composition containing the polymer of Example 1 was prepared by mixing 1 volume of composition A and 2 volumes of solution B with 10 volumes of 6% aqueous hydrogen peroxide solution, as follows:

| Ingredient | Composition A Weight Percent |
| --- | --- |
| Ammonium Persulfate | 80.0 |
| Sodium Silicate | 15.0 |
| Sodium Lauryl Sulfate | 5.0 |
|  | 100.0 |

| Ingredient | Solution B Weight Percent |
| --- | --- |
| Oleic acid | 35.0 |
| Ammonium hydroxide (29%) | 11.0 |
| Isopropanol | 15.0 |
| Polymer of Example 1 | 4.0 |
| Octylphenoxypolyethoxy(9–10) ethanol | 15.0 |
| Water | 20.0 |
|  | 100.0 |

The composition was applied to hair and allowed to stand for periods of time from 30 to 90 minutes depending upon the extent of bleaching desired. After rinsing and shampooing the hair displayed the same superior condition as was observed in the hair of the preceding examples, in contrast to the undesirable condition of hair bleached with a similar composition omitting the polymer.

EXAMPLE 5

A hair dyeing base composition containing the polymer of Example 1 was prepared by mixing 6% aqueous hydrogen peroxide with an equal volume of the following solution:

| Ingredient | Weight Percent |
| --- | --- |
| Oleic acid | 20.0 |
| Ammonium hydroxide (29%) | 7.6 |
| Octylphenoxypolyethoxy(9–10)ethanol | 20.0 |
| Isopropanol | 18.0 |
| Polymer of Example 1 | 5.0 |
| Ethylenediaminetetraacetic acid | 0.05 |
| Sodium Sulfite | 0.05 |
| p-Phenylenediamine | 0.1 |
| Resorcinol | 0.02 |
| Water to | 100.0 |

The composition was applied to the hair, allowed to stand about 20 minutes, rinsed with water and shampooed. The condition of the hair was markedly superior to that of hair treated with the same composition omitting the polymer, the differences being similar to those of the preceding examples.

EXAMPLE 6

An oxidative hair dyeing base composition containing our polymer was prepared by mixing 6% aqueous hydrogen peroxide with an equal volume of the following solution:

| Ingredient | Weight Percent |
| --- | --- |
| Oleic acid | 20.0 |
| Ammonium hydroxide (29%) | 7.6 |
| Octylphenoxypolyethoxy(9–10)ethanol | 20.0 |
| Isopropanol | 18.0 |
| Polymer of Example 1 | 5.0 |
| Ethylenediaminetetraacetic acid | 0.05 |
| Sodium sulfite | 0.05 |
| p-Phenylenediamine | 0.1 |
| Resorcinol | 0.02 |
| Water to | 100.0 |

The composition was applied to the hair, allowed to stand about 20 minutes at room temperature, rinsed with water and shampooed. The hair was dyed a light ash blonde color. In order to ascertain the presence of the conditioning effect, the following test is performed. Tresses are prepared using hair that has been bleached and waved. This type of hair is difficult to comb either wet or dry and represents a realistic standard for the evaluation of conditioning treatments. An untreated tress is marked as a control and is evaluated both for wet and dry combing properties. A number of tresses from the same hair lot (to eliminate variations from lot to lot) are then subjected to the hair treating composition to be tested. The evaluations are made by a panel of cosmetic scientists or beauty operators. The tresses are combed and ranked on a 1 to 5 scale, where 1 is the poorest and 5 is the best. The change in rating from the control value is an indication of the effectiveness of the conditioning treatment. Persistence of high ratings after a series of shampoos indicates the continued existence of conditioning on the tress. The ratings reported in the following examples are based on the above scale and are for wet combings unless specified otherwise. The condition of the hair treated with the composition of this Example 6 was markedly superior (rating 4) compared to that of hair treated with the same composition omitting the polymer (rating 2).

EXAMPLE 7

An aerosol oxidative hair dyeing composition was prepared to be used in a two compartment aerosol container described in U.S. Pat. No. 3,241,722:

| Ingredient | Weight Percent |
| --- | --- |
| Oleic acid | 8.7 |
| Monoethanolamine | 5.0 |
| Octylphenoxypolyethoxy(9–10)ethanol | 6.0 |
| Isopropanol | 25.0 |
| Ethylenediaminetetraacetic acid | 0.05 |
| Sodium Sulfite | 0.05 |
| Polymer of Example 1 | 1.0 |
| Sodium Chloride | 1.0 |
| p-Phenylenediamine | 0.1 |
| Resorcinol | 0.05 |
| Water to | 100.0 |

To 93 grams of the above composition was added 9.3 grams of 50/50 blend of propellants dichlorodifluoromethane and dichlorotetrafluoroethane. About 27 grams of a 16% aqueous hydrogen peroxide solution was placed in the inner compartment while the other composition together with the propellant mixture was placed in the outer compartment. Tresses dyed for 20 minutes at room temperature with this composition were a medium ash blonde. The condition of the tresses was excellent and persisted through at least four shampoos.

EXAMPLE 8

An aerosol oxidative hair dyeing composition was prepared and employed in the two compartment container described in U.S. Pat. No. 3,241,722. To 93 grams of the composition described below was added 9.3 grams of a 50/50 blend of propellants as described in Example 7 and placed in the outer portion of the container.

| Ingredient | Weight Percent |
| --- | --- |
| Oleic acid | 8.7 |
| Monoethanolamine | 6.7 |
| Isopropanol | 20.4 |
| Octylphenoxypolyethoxy(9–10)ethanol | 0.4 |
| Polymer of Example 1 | 0.5 |
| p-Phenylenediamine | 0.5 |
| Resorcinol | 0.3 |
| 2,4-diaminoanisole | 0.05 |
| p-aminophenol | 0.3 |
| Water - q.s. | 100.0 |

27 grams of 6.15% aqueous hydrogen peroxide was placed in the inner container. The above creamy composition was applied to blonde hair tresses, allowed to remain for 20 minutes at room temperature and rinsed. The tresses were dyed a dark ash brown. Conditioning was evaluated after shampooing and rated as 4.0.

EXAMPLE 9

An oxidative hair toning composition was prepared according to the following recipe and mixed with an equal weight of 6% aqueous hydrogen peroxide.

| Ingredient | Weight Percent |
|---|---|
| Triethanolamine | 7.0 |
| Isopropanol | 16.0 |
| Polymer of Example 1 | 2.0 |
| Polyoxyethylene(2)oleyl ether | 18.0 |
| Polyoxyethylene(10)oleyl ether | 2.0 |
| Ethylenoxide(12)condensate of a C-18 fatty amine | 10.0 |
| Sodium Oleate | 5.0 |
| p-Phenylenediamine | 0.25 |
| Resorcinol | 0.05 |
| Water to | 100.0 |

After 20 minutes contact at room temperature with blonde hair followed by rinsing and shampooing, the tress was toned a medium ash blonde. A combing evaluation rated the hair 3.5. A control without the polymer was rated 2.2. After two weeks, the original tress was again shampooed and evaluated and was rated at 3.2.

EXAMPLE 10

An aerosol oxidative hair dyeing composition was prepared and employed in the two compartment container described in U.S. Pat. No. 3,241,722. To 93 grams of the composition described below was added 9.5 grams of a 50/50 mixture of propellants as described in Example 7; the mix was placed in the outer portion of the container. 27 grams of aqueous hydrogen peroxide (6%) was placed in the inner container.

| Ingredient | Weight Percent |
|---|---|
| Oleic Acid | 17.4 |
| Octylphenoxypolyethoxy(9-10)ethanol | 2.0 |
| Isopropanol | 15.0 |
| Monoethanolamine | 6.9 |
| Polymer of Example 1 | 0.6 |
| p-Phenylenediamine | 0.06 |
| Resorcinol | 0.06 |
| Water q.s. to | 100.0 |

Blonde hair tresses were treated with the creamy composition discharged from the container, being left in contact with it at room temperature for 25 minutes, rinsed and shampooed. The hair was dyed to a light ash blonde. The tresses were combed and rated 4.5. A similar composition without the polymer produced a rating of 2.0 on similarly treated tresses.

EXAMPLE 11

A permanent hair color was prepared using oxidation dye intermediates without hydrogen peroxide:

| Ingredient | Weight Percent |
|---|---|
| Polydiallyldiethylammonium Chloride | 3.0 |
| Hexylene Glycol | 10.0 |
| Sodium Chloride | 1.0 |
| Sodium Coco-N-methyltauride | 5.0 |
| p-Phenylenediamine | 3.0 |
| p-Aminophenol | 1.0 |
| Resorcinol | 0.5 |
| Water q.s. to | 100.0 |

The two phase product was shaken before use and applied to blonde tresses for 15 minutes. The hair was rinsed and found to be dyed an ashen light brown. After two shampoos the combing rating was still 4.5.

EXAMPLE 12

A disperse dye composition for dyeing human hair was prepared and evaluated on blonde bleached/waved tresses.

| Ingredient | Weight Percent |
|---|---|
| Polyoxyethylene(23)lauryl ether | 5.00 |
| Lauric diethanolamide | 5.00 |
| C. I. Disperse Black, C. I. No. 11365 | 1.00 |
| Polydiallyldimethylammonium chloride (viscosity 500 cps.) | 20.00 |
| Isopropanol | 25.00 |
| Perfume | 0.10 |
| Water q.s. to | 100.0 |

After 30 minutes contact with the composition, the hair was dyed a golden blonde. After two shampoos, the combing rating of the hair was still 4.0.

EXAMPLE 13

The following disperse dye composition for dyeing human hair was prepared and evaluated on blonde bleached/waved tresses.

| Ingredient | Weight Percent |
|---|---|
| Polydiallyldimethylammonium chloride (viscosity 128000 cps.) | 20.00 |
| Sodium Chloride | 1.00 |
| Benzyl Alcohol | 4.00 |
| C. I. Disperse Black 1, C. I. No. 11365 | 1.00 |
| Sodium lauroylsarcosinate | 13.17 |
| Perfume | 0.1 |
| Water q.s. to | 100.00 |

The composition was applied and worked up to a lather on tresses and allowed to stand for 30 minutes. Water was applied and worked up to a lather again and rinsed. The hair was dyed a golden blonde and after two shampoos, had a wet rating of 4.0.

EXAMPLE 14

A basic dye hair toning composition was prepared and evaluated on bleached - waved hair.

| Ingredient | Weight Percent |
|---|---|
| Stearyldimethylbenzylammonium chloride | 1.8 |
| Polymer of Example 1 | 4.5 |
| Methylene Blue | 0.045 |
| Hexylene Glycol | 25.00 |
| Polyethyleneoxide, M.W. 100,000 | 0.45 |
| Perfume | 0.1 |
| Water q.s. to | 100.0 |

Bleached-waved hair was treated for 30 minutes, water-rinsed, and shampooed. The hair was toned a pleasant pale green, actually blue on a yellow substrate, and after two shampoos was rated 3.25.

EXAMPLE 15

A hair lightener composition was prepared having the following composition. Lighteners usually produce roughened hair and conditioning in these systems is particularly advantageous.

| Ingredient | Weight Percent |
| --- | --- |
| Oleic Acid | 20.00 |
| 2-Amino-2-methyl-1-propanol | 9.31 |
| Polymer of Example 1 | 5.00 |
| Ethanol | 10.00 |
| Perfume | 0.20 |
| Water q.s. to | 100.0 |

To one part by weight of the above composition was added two parts of aqueous 6% hydrogen peroxide and the mixture was applied to brown hair for 30 minutes. The hair was water-rinsed and found to be lightened about one shade and was readily combed. Using the same composition on bleached-waved hair, the conditioning was found to be 4.5 to 5.0 after two shampoos.

EXAMPLE 16

The same composition was prepared as in Example 15 except that instead of mixing in two parts of the hydrogen peroxide solution there was mixed in 0.5% by weight of C.I. Basic Brown 2 (C.I. No. 21030). The composition was applied to white hair for 30 minutes, rinsed and shampooed. The hair was colored a light auburn. Bleached-waved hair to which the same composition was applied had a combing rating of 5.0 after two shampoos.

EXAMPLE 17

The following conditioning acid dye composition was prepared and evaluated on white hair.

| Ingredient | Weight Percent |
| --- | --- |
| Miranol C2M Conc* | 8.00 |
| Polymer of Example 1 | 5.00 |
| F.D. & C Blue No. 2, C. I. No. 73015 | 0.50 |
| Benzyl alcohol | 4.50 |
| Perfume | 0.10 |
| Water q.s. to | 100.0 |

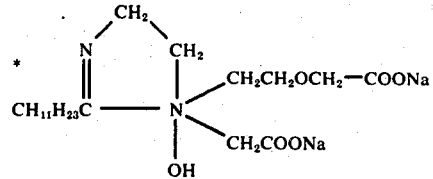

The composition was applied to white hair for 30 minutes after which a lather was worked up. After rinsing, the hair was found to be toned a pale blue. The color was only semi-permanent and much was removed after two shampoos. Evaluation of the composition on bleached-waved hair after two shampooings showed a rating of 4.5 to 5.0.

EXAMPLE 18

The following aerosol basic-dye hair conditioning composition was prepared and evaluated on white hair for color and condition.

| Ingredient | Weight Percent |
| --- | --- |
| Polydipropyldiallylammonium chloride | 4.0 |
| Ethanol | 85.9 |
| Condensate of 10% ethylene oxide and 90% propylene oxide with propylene glycol (M.W. about 1100) | 10.0 |
| Methylene Blue | 0.10 |

Ninety parts by weight of the above composition are packaged with 10 parts of propellant mixture consisting of trichloromonofluoromethane 45%, dichlorodifluoromethane 45% and isobutane 10%, in an aerosol container. The container was shaken prior to use and the composition was applied to damp hair and left for 30 minutes then water-rinsed and shampooed. The hair was dyed a light blue. After two shampoos, the condition of the hair was still rated 3.0.

EXAMPLES 19–21

The following compositions (Table I) were prepared with four different polymers, the compositions being suitable for use as hair dyes by the addition of the conventional desired dye. The compositions, each containing a different polymer, were then mixed with an aqueous 16% hydrogen peroxide solution in the proportion of 3.5 parts by weight of the composition to 1.0 part of peroxide solution, and the mixture left in contact with hair tresses, one virgin hair which had never been bleached or chemically waved, the other bleached and waved hair, for 20 minutes at room temperature, then rinsed.

Each hair tress was then rated for condition with the results set forth in Table II. In this case the hair tresses were rated both while wet (WC) and after drying (DC) as well as being rated again after one shampoo and rinse (1S) and after three (3S).

Table I

| Ingredient | Percent by Weight |
| --- | --- |
| Oleic acid | 8.7 |
| Monoethanolamine | 5.0 |
| Triton X-100 (Octylphenoxypolyethoxy (9–10)ethanol) | 1.0 |
| Triton X-35 (Octylphenoxypolyethoxy (3–4)ethanol) | 5.0 |
| Isopropanol | 25.0 |
| EDTA | 0.05 |
| Sodium sulfite | 0.05 |
| Polymer | 1.0 |
| Water | q.s. |

Table II

| Polymer | Hair Condition | | | | | | | |
| --- | --- | --- | --- | --- | --- | --- | --- | --- |
| | Virgin | | | | Bleached/Waved | | | |
| | WC | DC | WC(1S) | WC(3S) | WC | DC | WC(1S) | WC(3S) |
| Polymer of Example 1 | 4.5 | 3.5 | 4.5 | 4.0 | 4.3 | 4.0 | 4.0 | 3.0 |
| Polydipropyldiallylammonium chloride | 4.0 | 3.0 | 3.5 | 3.5 | 2.8 | 4.0 | 2.5 | 2.5 |
| Polydiallylpiperidinium chloride | 4.5 | 3.0 | 4.5 | 3.5 | 4.3 | 4.0 | 3.5 | 2.5 |
| Polydiallylamine | | | | | | | | |

Table II-continued

| Polymer | Hair Condition | | | | | | | |
| --- | --- | --- | --- | --- | --- | --- | --- | --- |
| | Virgin | | | | Bleached/Waved | | | |
| | WC | DC | WC(1S) | WC(3S) | WC | DC | WC(1S) | WC(3S) |
| hydrochloride | 4.5 | 3.0 | 4.5 | 4.0 | 4.3 | 3.5 | 4.0 | 3.0 |
| None | 3.5 | 3.0 | 3.5 | 3.5 | 2.5 | 4.0 | 2.5 | 2.5 |

EXAMPLES 22–32

Hair bleaching compositions were prepared by mixing with one part by weight of a 16% aqueous hydrogen peroxide solution 3.5 parts of each of several compositions having the following recipe, the polymer in each case being different as listed in Table III.

Recipe

| Ingredient | Weight Percent |
| --- | --- |
| Oleic acid | 9.0 |
| Monoethanolamine | 5.1 |
| Octylphenoxypolyethoxy(9–10)ethanol | 1.0 |
| Octylphenoxypolyethoxy(3–4)ethanol | 5.0 |
| Isopropanol | 15–37 |
| Cationic polymer | 1.0 |
| Water q.s. to | 100.0 |

Table III

Polydimethyldiallylammonium chloride
Polydiallylamine hydrochloride
Polydipropyldiallylammonium chloride
Polydiallylpiperidinium chloride
Copolymer (50:50) of dimethyldiallylammonium chloride and acrylamide
Copolymer (75:25) of dimethyldiallylammonium chloride and acrylamide
Copolymer (27:63) of dimethyldiallylammonium chloride and acrylamide
Copolymer (13:87) of dimethyldiallylammonium chloride and acrylamide
Copolymer (7:93) of dimethyldiallylammonium chloride and acrylamide
Copolymer (90:10) of dimethyldiallylammonium chloride and diacetone acrylamide
Copolymer (95:5) of dimethyldiallylammonium chloride and diacetone acrylamide The compositions were evaluated by applying them to tresses of both virgin and bleached/waved hair and allowing them to stand for 20 minutes. After rinsing and shampooing, the tresses displayed the same superior condition as observed in the other examples in contrast to the undesirable condition of tresses treated with similar compositions omitting the polymer.

Also useful in the present invention in addition to the polymers and copolymers specifically described above are various other polymers and copolymers described in U.S. Pat. Nos. 3,288,770 and 3,412,019; particularly effective are a homopolymer of methyl-beta-propionamidodiallylammonium chloride as well as a copolymer made from 75:25 by weight mixture of dimethyldiallylammonium chloride and of methyldodecyldiallylammonium chloride and a copolymer made from a 50:50 by weight mixture of these monomers. These polymers and copolymers can be substituted in the foregoing examples with only slight differences in degree of effectiveness of the resultant cosmetic composition.

What is claimed is:

1. A hair coloring composition containing, in addition to a coloring agent, water and a water soluble polymer having a molecular weight from 20,000 to 3,000,000 and having a molecular chain containing units selected from the group consisting of

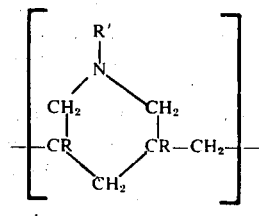

and

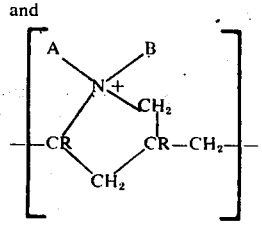

wherein R is hydrogen or methyl; R' is hydrogen, alkyl having one to twenty-two carbon atoms, lower hydroxyalkyl having from one to five carbon atoms, or lower alkyl containing a terminal amido group; and A and B are independently alkyl having from one to twenty-two carbon atoms, lower hydroxyalkyl, or lower alkyl containing a terminal amido group, or wherein A and B taken together with N are piperidinyl or morpholinyl, the amount of said polymer being from 0.05% to 40% by weight of the total composition.

2. The composition for coloring hair as claimed in claim 1 containing as the coloring agent a member selected from the group consisting of a hair dye and an oxidative hair dye intermediate in an amount from 0.03 to 10% by weight of the total composition.

3. The composition as claimed in claim 2 containing in addition
a surface active agent in an amount from 0.1 to 50% by weight of the total composition and
a water miscible hydroxylated aliphatic solvent sufficient to solubilize all of the ingredients, the amount of said solvent being from 1 to 90% by weight of the total composition.

4. The composition as claimed in claim 3 in which A and B are both methyl.

5. The composition as claimed in claim 3 in which A and B are both ethyl.

6. The composition as claimed in claim 3 in which the polymer contains in addition up to 95% by weight of the total of units selected from the group consisting of

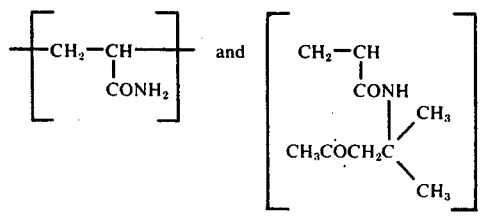
7. The composition as claimed in claim 6 in which A and B are both methyl.
8. The composition as claimed in claim 3 in which the polymer is polydiallyldiethylammonium chloride.
9. A process of coloring the hair which comprises applying thereto an effective amount of the composition as claimed in claim 1.
* * * * *

UNITED STATES PATENT OFFICE
CERTIFICATE OF CORRECTION

Patent No. 3,986,825                        Dated October 19, 1976

Inventor(s)   Phillip E. Sokol

It is certified that error appears in the above-identified patent and that said Letters Patent are hereby corrected as shown below:

Column 1, line 17, "Because" is misspelled;

Column 8, line 25, change "lotion of hair" to --lotion to hair--;

Column 16, line 30, change the formula to read as follows:

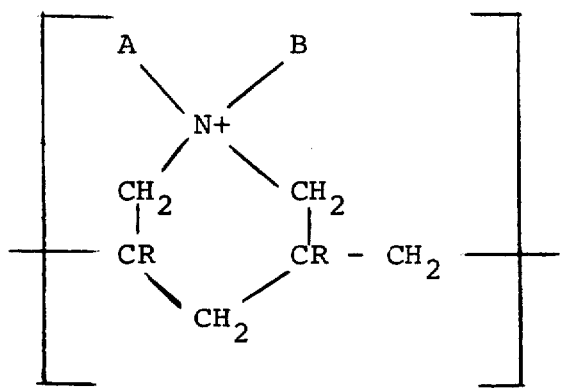

Signed and Sealed this

Eighteenth Day of January 1977

[SEAL]

Attest:

RUTH C. MASON
Attesting Officer

C. MARSHALL DANN
Commissioner of Patents and Trademarks